US006420603B1

(12) United States Patent
Alessandroni et al.

(10) Patent No.: US 6,420,603 B1
(45) Date of Patent: Jul. 16, 2002

(54) PROCESS FOR THE PREPARATION OF N, N'-BIS[2,3-DIHYDROXYPROPYL]-5-[(HYDROXYACETYL) METHYLAMINO]-2, 4, 6-TRIIODO-1, 3-BENZENEDI CARBOXAMIDE

(75) Inventors: Laura Alessandroni; Patrizia Ambrosetti; Maria Argese; Renato Geremia; Enrico Moretti; Vittorio Valle; Giorgio Ripa; Marcella Murru, all of Milan (IT)

(73) Assignee: Bracco International B.V., Amsterdam (NL)

( * ) Notice: Subject to any disclaimer, the term of this patent is extended or adjusted under 35 U.S.C. 154(b) by 0 days.

(21) Appl. No.: 09/856,554

(22) PCT Filed: Nov. 25, 1999

(86) PCT No.: PCT/EP99/09118

§ 371 (c)(1),
(2), (4) Date: Jul. 17, 2001

(87) PCT Pub. No.: WO00/32561

PCT Pub. Date: Jun. 8, 2000

(30) Foreign Application Priority Data

Nov. 27, 1998 (IT) .......................................... MI98A2574

(51) Int. Cl.⁷ ............................................ C07C 241/00
(52) U.S. Cl. ........................ 564/123; 564/152; 564/123; 560/9; 560/13; 560/16; 560/27; 560/30; 562/430; 562/432; 562/443

(58) Field of Search ................................. 564/123, 152, 564/134; 560/13, 9, 16, 27, 30; 562/430, 432, 443

(56) References Cited

U.S. PATENT DOCUMENTS 5,066,823 A * 11/1991 Felder et al. .................. 560/13

FOREIGN PATENT DOCUMENTS

EP      0 185 130      6/1986
WO    WO88/09328    12/1988

OTHER PUBLICATIONS

Annnelli et al, Tetrahedron, vol. 53, No. 34, pp. 111919–11928.*
Anelli P. L. et al.: "Smiles Rearrangement as a Tool for the Preparation of 5–'(2–Hydroxyacyl)amino!–2,4,6–triiodo–1, 3–benzenedicarboxamides: Main Pathway and Side Reactions" Tetrahedron, N., Elsevier Science Publishers, Amsterdam, vol. 53, No. 34, pp. 11919–11928.

* cited by examiner

*Primary Examiner*—Paul J. Killos
*Assistant Examiner*—Héctor M. Reyes
(74) *Attorney, Agent, or Firm*—Nixon & Vanderhye P.C.

(57) ABSTRACT

A novel process for the preparation of N,N'-bis[2,3-dihydroxypropyl]-5-[(hydroxyacetyl) methylamino]-2,4,6-triiodo-1, 3-benzenedi carboxamide of formula (I), commonly known as lomeprol, a novel non-ionic contrast agent which shows very good safety and contrast effectiveness.

11 Claims, No Drawings

PROCESS FOR THE PREPARATION OF N, N'-BIS[2,3-DIHYDROXYPROPYL]-5-[(HYDROXYACETYL) METHYLAMINO]-2, 4, 6-TRIIODO-1, 3-BENZENEDI CARBOXAMIDE

The present invention relates to a novel process for the preparation of N,N'-bis[2,3-dihydroxypropyl]-5-[(hydroxyacetyl)methylamino]-2, 4,6-triiodo-1,3-benzenedicarboxamide of formula (I), commonly known as Iomeprol, a novel non-ionic contrast agent which shows excellent safety and contrast effectiveness.

The synthesis of the compound of formula (I) was described first in EP 26,281, but the subsequent EP 365,541 suggested a different synthetic route, based on a Smiles' rearrangement reaction of 5-alkoxy-2,4,6-triiodo-1,3-benzenedicarboxamide derivatives in basic aqueous conditions, to give the corresponding 5-(hydroxyacyl)amino derivatives, according to Scheme 1 (see below).

The advantages of the latter synthesis over that described in EP 26,281 mainly derive from avoiding some reagents and solvents such as: thionyl chloride, acetic anhydride, methyl iodide, methylene chloride and chloroform, as well as reactions (such as the catalytic reduction with hydrogen), which under industrial production conditions are environmentally and toxicologically dangerous therefore requiring specific operative conditions.

The key intermediate of this synthetic route is the compound of formula (VII), which is synthesized as described in EP 185,130 and reported in Scheme 1.

Scheme 1

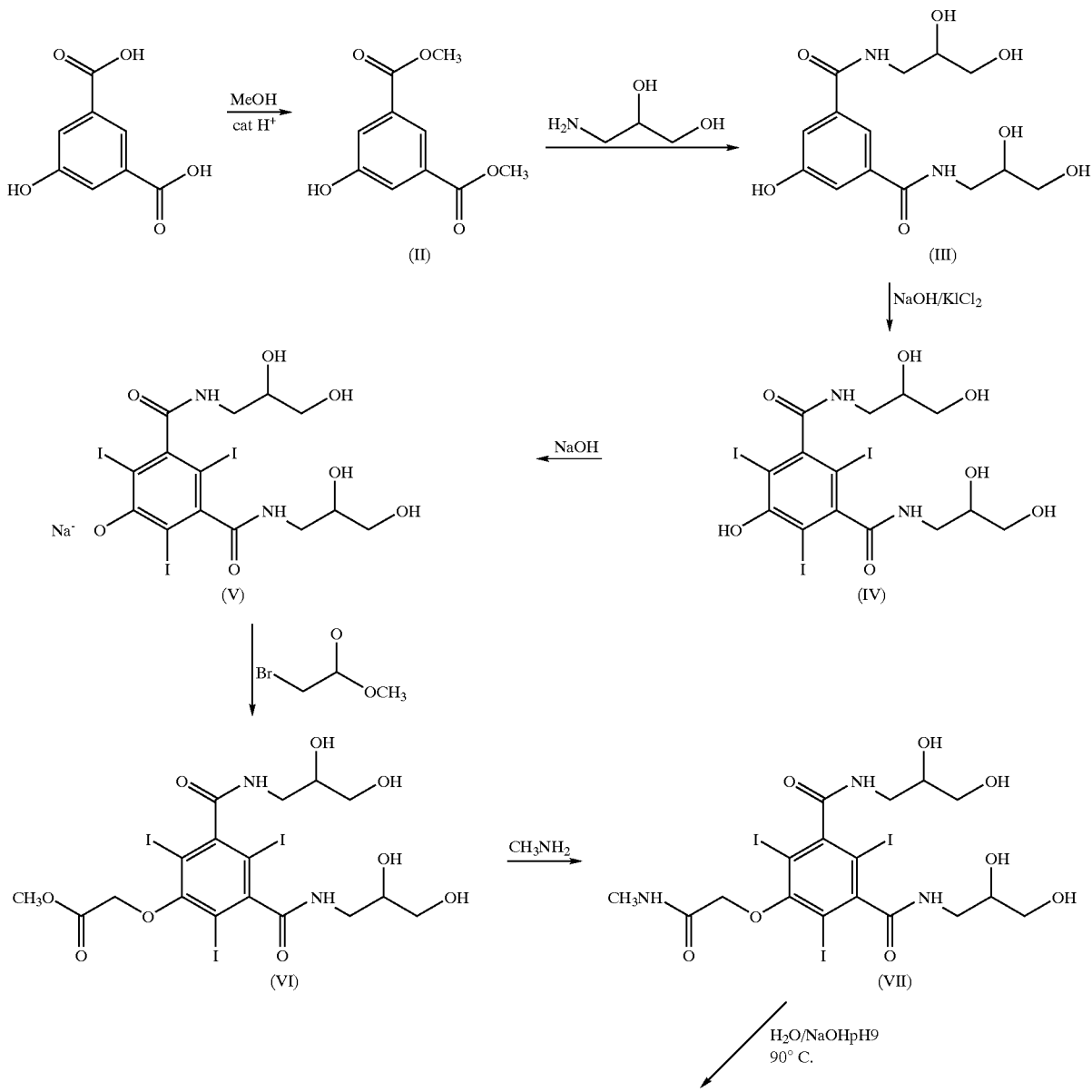

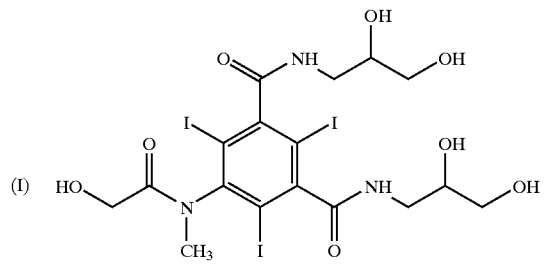

The process comprises the use of 5-hydroxy-1,3-benzenedicarboxylic acid as starting compound, which is esterified under usual conditions with MeOH and acidic catalysis to methyl diester of formula (II). The latter is hot amidated with 1-amino-2,3-propanediol (commonly named isoserinol), with a 100% reagent excess. Methanol formed during the reaction is distilled and the amine excess is removed by means of a strong cationic resin to give the compound of formula (III). The resulting diamide is iodinated in aqueous basic solution with a 2.5M KICl$_2$ solution to give the compound of formula (IV).

No details are given concerning the recovery conditions of compound (IV) which is transformed into the corresponding sodium salt (V), then reacted while hot is methyl bromoacetate in dimethylacetamide to give, after recrystallization from methanol, the compound of formula (VI), which is subjected to amidation with hot methylamine to yield compound (VII). EP 185,130 discloses compound (VII) as an intermediate for the synthesis of a number of contrast agents deriving from N,N'-bis(2,3-dihydroxypropyl)-2,4,6-triiodo-5-hydroxy-1,3-benzenedicarboxylic acid amide.

Scale-up of this process shows, however, unexpected technical problems, thus summarized:

in the formation of dimethyl ester of formula (II), as it is well known in literature, due to the characteristics of methanol, a non-catalytic amount of H$_2$SO$_4$ is needed to shift the equilibrium towards the formation of the ester. Under these conditions, monomethyl sulfate forms as a side-product which, analogously to the well-known dimethyl sulfate, is dangerous for the health;

compound (IV), as well as the sodium salt of formula (V), has to be isolated from the aqueous solution;

the alkylation of compound (V) with methyl bromoacetate has to be carried out in dimethylacetamide, which should be recycled for economic reasons;

compound (VI) has to be purified by crystallization from methanol;

in the described iodination conditions, an excess amount of iodine has to be used, to the detriment of the subsequent synthetic step, in that such an excess can act as an oxidizer towards the alcohol moiety present in the amides at the 3- and 5-positions to give the following compound

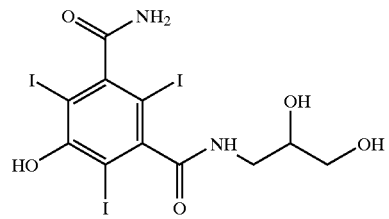

which is hardly separable from compound (IV) and which, after the subsequent synthetic steps, produces an impurity which contaminates the final product, Iomeprol. This impurity is considerably toxic and its formation should therefore be prevented as much as possible.

For the purpose of making industrial syntheses more environmentally safe, avoiding the use of organic solvents as much as possible, while preventing the formation of side-products dangerous for health, a safe alternative process for the preparation of (VII) has been searched for.

It is therefore the object of the present invention a novel process for the preparation of Iomeprol, comprising the steps represented in the following Scheme 2:

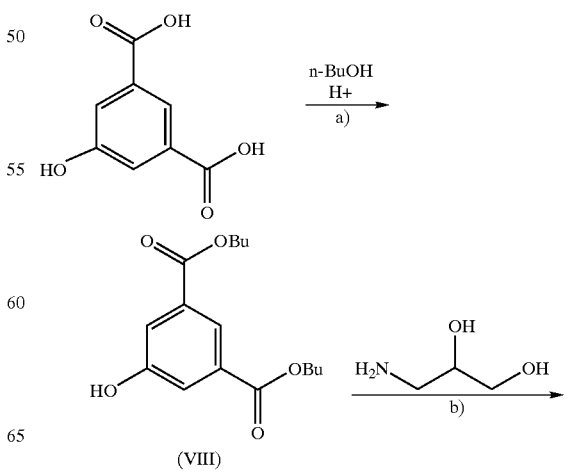

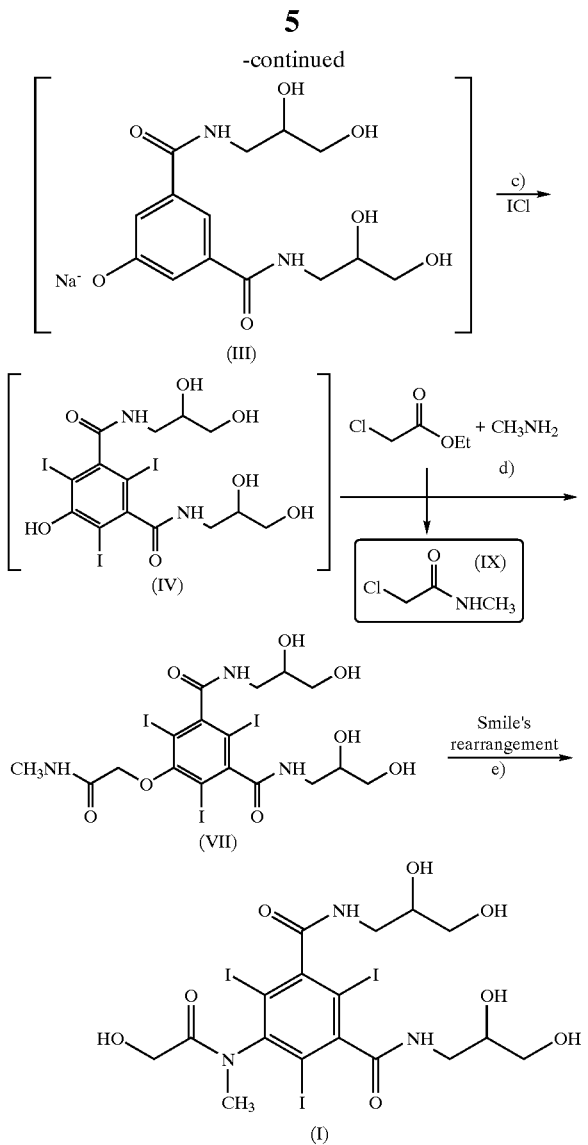

a) esterification with butanol and acidic catalysis to give 5-hydroxy-1,3-benzenedicarboxylic acid butyl diester (VIII);

b) amidation of compound (VIII) with an isoserinol excess, to give an aqueous solution of N,N'-bis-(2,3-dihydroxypropyl)-5-hydroxy-1,3-benzene-dicarboxamide (III);

c) iodination of compound (III) with ICl, in stoichiometric amounts or in a 1% excess, to give N,N'-bis-(2,3-dihydroxypropyl)-5-hydroxy-2,4,6-triiodo-1,3-benzenedicarboxamide (IV);

d) alkylation of compound (IV) with compound (IX), 2-chloro-N-methyl-acetamide, in aqueous solution, to give N,N'-bis(2,3-dihydroxypropyl)-2,4,6-triiodo-5-[2-(methylamino)-2-oxoethoxy]-1,3-benzene-dicarboxamide (VII), which is used as humid product; finally, e) Smiles' rearrangement of compound (VII) in basic conditions and subsequent purification to give Iomeprol (I).

A further object of the present invention is the process for the preparation of compound (VII), an useful intermediate for the preparation of iodinated contrast agents as described in EP 185,130, comprising steps a), b), c) and d), and further the final drying (VII).

Contrary to what disclosed in EP 185,130, the process of the present invention is characterized in that all synthetic steps b) to e), including the preparation of the alkylating agent of formula (IX), are carried out in aqueous solution, in that organic solvents are avoided and in that the recovery of the single intermediates is no longer necessary, but it is possible to operate continuously directly on the solutions of the intermediates themselves.

In step a) the formation of the butyl diester of formula (VIII) allows to successfully overcome the problems cited above. In fact operating according to the process of the invention it is possible to use a catalytic amount of $H_2SO_4$, preferably corresponding to 6% by mol on 5-hydroxy-1,3-benzenedicarboxylic acid.

Alternatively, a catalytic amount of p-toluenesulfonic acid monohydrate can be used, preferably in amounts equivalent to 6% by mol on 5-hydroxy-1,3-benzenedicarboxylic acid. The esterification reaction can also be carried out in the hot and operating under gradually decreasing reduced pressure, instead at atmospheric pressure.

Compound (VIII) can be recovered either by direct crystallization form the final reaction mixture, previous concentration, or by precipitation from an alkali aqueous solution, previous elimination of the organic solvent. In the first case, the final crystallization is carried out in the cold (T of about 5° C.), and more crops have to be recovered through repeated concentrations of mother liquors, or mother liquors of the first crop have to be recycled and used for a subsequent esterification reaction. In the second case (recovery from an alkaline aqueous solution) the reaction mixture is concentrated to a residue, which is subsequently treated with an aqueous solution of an inorganic base (preferably sodium or potassium hydroxide or ammonia): by controlled cooling of the resulting emulsion, compound (VIII) is obtained as a partially crystalline solid. Compound (VIII) can be filtered or centrifuged or filter-pressed and dried.

Alternatively, compound (VIII) can be redissolved in n-butanol and the resulting solution can be used in the subsequent step b). The advantages of the direct use of the solution are the possibility to avoid the recovery step of the humid product as well as, above all, the drying step, which requires a prolonged treatment in static dryer under vacuum at 30–40° C., compound (II) being a low-melting solid.

Step b) is substantially equivalent to that described in the above Patent, and consists in the amidation of compound (VIII) with isoserinol.

The reaction is carried out in the melted state, (i.e. in a 120% isoserinol excess), at a temperature of 90–95° C., for a time of about 12 hours, removing the formed n-butanol by distillation under vacuum. When using the butanol solution of compound (VIII), the solvent is removed before the reaction to obtain compound (VIII) as a melted residue, which is finally added with isoserinol. At the end of the reaction the mass is taken up with water, to obtain an aqueous solution of compound (III), in the form of phenol, which is purified from the isoserinol excess through a cation exchange resin. The eluates are finally concentrated and adjusted to pH 9–10 by addition of sodium hydroxide thereby obtaining the aqueous solution of the sodium salt corresponding to compound (III).

The excess isoserinol is suitably recovered and recycled in the process by elution from the resin with a diluted ammonia solution. The solution is concentrated to a residue and then purified by formation of isoserinol oxalate in ethanol solution, as described in Italian Patent application MI 97 A 000782. The salt is filtered and then dissolved in water. The solution is purified through a strongly acidic polystyrene matrix cationic exchange resin and isoserinol is recovered by elution with a diluted ammonia solution. The solution containing the recovered isoserinol is concentrated to a residue.

Alternatively, step b) can be carried out without recovering the butyl diester obtained at step a). In this case, at the end of the amidation reaction of compound (VIII) with isoserinol, after dilution with water, the reaction mixture is purified from the isoserinol excess by chromatography on a first column containing a strongly acidic cation exchanger and from the anionic impurities by chromatography on a second column containing a weakly basic anion exchanger, connected in series with the first column. The strongly acidic cation exchange resin is selected from those commercially available, such as Rohm & Haas Amberjet® 1200H and the weakly basic anions exchanger one is, for example, Diaion Relite® MGl.

Iodination is carried out using ICl as iodinating agent (44.5% $I_2$ in HCl solution) in aqueous neutral medium, in a very narrow pH range from 6 to 7, by addition of dibasic sodium phosphate or $CaCO_3$ in excess, at room temperature. It has, in fact, been observed that at pH>7 the Smiles' rearrangement, characteristic of step e), already takes place, and therefore the final compound (I) forms in part. It is however convenient to make use of the ability of compound (VII) to crystallize from water at this step to effectively remove all the impurities form the preceding synthetic steps.

One of the most important aspects of the process of the invention is the control of the amount of iodinating agent, which is obtained innovatively and is particularly simple for use even at an industrial scale, by a potentiometer. Under these conditions the oxidizer excess can be minimized (to about 1%) thereby avoiding undesired oxidation side-reactions.

The iodinating agent necessary is substantially equivalent to the stoichiometric amount or to a small excess (about 1%), and the excess is then destroyed with sodium bisulfite. The resulting solution is directly subjected to the alkylation step d), thus avoiding a step by using the amido derivative preformed in the nucleophilic substitution on the free phenol group of compound (IV), instead of an ester derivative, as disclosed in EP 185,130.

In particular, considering the technical teachings of U.S. Pat. No. 5,763,663, the whole synthesis can be one step shorter. Said Patent, in fact, discloses the direct reaction of the phenol precursors with a reactive compound already containing the desired amido group. The cited Patent, anyhow, only describes the use of the process for the preparation of an intermediate for the synthesis of S-N,N'-bis[2-hydroxy-1-(hydroxymethyl)ethyl]-5-[(2-hydroxy-1-oxopropyl)amino]-2,4,6-triiodo-1,3-benzenedicarboxamide, known under the commercial name Iopamidol. Said intermediate is, of course, not useful for the preparation of Iomeprol, which is the object of the present invention.

The alkylation of compound (IV) with compound (IX) takes place at about pH 6 and at a temperature of 95° C., being the alkylating agent added in amounts of 1.8–2.2 mol per mol of substrate. At the end of the reaction, which usually requires 7 hours, the resulting suspension is cooled and fed to the isolation step of compound (VII).

Alternatively, the iodination reaction can be carried out without a buffer, keeping pH at the desired values (between 6 and 7) by addition of NaOH.

In this case the alkylation of compound (IV) with compound (IX) is also carried out keeping pH at about 6 by addition of sodium hydroxide, at a temperature of 95° C.

The alkylating agent (IX) is prepared by direct reaction of ethyl chloroacetate and methylamine (40% aqueous sol.), which is added to ethyl chloroacetate keeping temperature from −10° C. to 0° C. Methylamine is added in a slight excess (5–15%). The reaction usually requires 30 minutes; at the end the mixture is diluted with water and pH is adjusted to acidic values (between 2 and 5). The resulting aqueous solution of compound (IX), has an about 30% w/w concentration and can be used directly in the alkylation step.

Step e) can be conveniently effected under the conditions disclosed in EP 365,541.

Particularly preferred is the purification of the final solution according to the procedure described in WO 97/30788 using a specific device designed for regenerating mixed beds of ion exchange resins, including cation exchange resins and anion exchange resins. Alternatively, the final purification of compound (I) can be carried out according to the procedure described in WO 98/56504, example 5.

Moreover, at the end of the rearrangement, pH of the solution can be adjusted to 5.5 by removing the sodium hydroxide present by means of a weakly acidic cationic resin, instead of adding hydrochloric acid. The preparation is reported in detail in the Experimental Section.

The following example illustrates the best experimental conditions to carry out the process of the invention.

EXPERIMENTAL SECTION

Example 1

Preparation of Compound (VII) N,N'-Bis(2,3-dihydroxypropyl)-2,4,6-triiodo-5-[2-(methylamino)-2-oxoethoxy]-1,3-benzenedicarboxamide A) Preparation of 5-Hydroxy-1,3-benzenedicarboxylic Acid Butyl Diester The esterification reactor, is loaded under nitrogen with 101.7 kg of n-butanol and 62 kg (320 mol) of 5-hydroxy-1,3-benzenedicarboxylic acid. 2 kg of concentrated sulfuric acid are added under stirring. The resulting suspension is heated to ebullition of the solvent, removing water by azeotropical distillation: about 1.5 h after the starting of heating a clear solution is obtained, which is heated for a further 3 h. After completion of the reaction the solution is cooled to a 50° C. and concentrated under vacuum to obtain the desired product as a melted residue. Keeping the temperature of the residue above 70° C., a 0.15M NaOH solution is dropped therein, to obtain an emulsion of the melted final compound dispersed in water, whose pH is adjusted to 8.5 with 0.15M NaOH. The emulsion is cooled to 43° C. under strong stirring, seeded with 1 kg (3.3 mol) of the final compound crystallized from water and slowly cooled to 28° C. The resulting suspension is cooled to 17° C. and then filter-pressed, washing the solid with water to neutral.

The humid product is directly redissolved in the filter-press with n-butanol. A solution is obtained weighing about 280 kg, containing 96–97 kg (326–330 mol) of the desired compound.

Yield: 95–96%.

B) Preparation of N,N'-Bis-(2,3-dihydroxypropyl)-5-hydroxy-1,3-benzenedicarboxamide The condensation between 41.6 kg (141.3 mol) of the compound prepared at step A) and 56.8 kg (623.4 mol) of isoserinol is carried out in a reactor equipped with stirrer, at a temperature of about 90–95° C. When the reaction is completed the final solution is diluted with water and purified through a strongly acidic polystyrene matrix ion exchange cationic resin, to remove the isoserinol excess, eluting with water. The eluate from the column is concentrated to a standard volume, then alkalinized with a sodium hydroxide solution, which is added to obtain the solution of the corresponding sodium salt.

227.5 kg of 20% solution containing 45.4 kg (138.6 mol in phenol form) of the desired compound are thereby obtained.

Yield 97.9%; HPLC assay: >98% (Area).

Isoserinol is easily recovered by elution from the resin with a diluted ammonia solution. The solution is concentrated to a residue and then purified. Isoserinol is salified with oxalic acid in ethanol solution. The salt is filtered and then dissolved in water. The solution is purified through a strongly acidic polystyrene matrix ion exchange cationic resin and isoserinol is recovered eluting with a diluted ammonia solution. The solution containing the recovered isoserinol is concentrated to a residue.

Yield: 76.3%.

C) Preparation of 2-Chloro-N-methyl-acetamide

The condensation of 34.5 kg (283 mol) of ethyl chloroacetate and 24 kg (310 mol) of monomethylamine (40% aqueous solution) is carried out in a reactor kept at a temperature of −5° C. After completion of the addition of the amine the solution is kept at steady temperature for a further 30 minutes, then diluted with 40.5 kg of water and pH is adjusted to acidic values (pH<5), to obtain a 30% aqueous solution (99 kg), containing 29.7 kg (276.2 mol) of 2-chloro-N-methylacetamide.

Yield: 98%.

D) Preparation of N,N'-Bis(2,3-dihydroxypropyl)-2,4,6-triiodo-5-[2-(methylamino)-2-oxoethoxy]-1,3-benzenedicarboxamide 227.5 kg of solution (corresponding to 45.5 kg of dry product in the phenol form; 138.6 mol) obtained at step B) are diluted with 50 kg of water and added with 10 kg of anhydrous dibasic sodium phosphate. At the same time ICl (44.5% $I_2$ aqueous solution) and a 30% sodium hydroxide solution are added, keeping pH at 7. The addition ends when the redox potential is stabilized at 500 mV. 120 kg of ICl and 107 kg of sodium hydroxide are loaded in total.

After that, 2.5 kg of sodium bisulfite are added to destroy the iodine excess and the potential decreases to −20 mV.

18.5 kg of anhydrous dibasic sodium phosphate and 99 kg of the solution of 2-chloro-N-methyl-acetamide (276.2 mol) prepared at step C) are added, pH is adjusted to 6.2 by addition of 3 kg of HCl. The mixture is heated at 95° C. and stirred for 7 hours, then cooled to 60° C. and diluted with 50 kg of water. The final suspension is repeatedly filter-pressed, washing the solid with water.

130 kg of the desired humid product are thereby obtained, equivalent to 90 kg of the dry product (115.8 mol).

Yield: 83.6%.

E) Preparation of Compound (I)

90 kg of the compound prepared at step D), are suspended in 400 L of deionized water and refluxed. The suspension is added with 310 g of 30% (w/w) sodium hydroxide, then heated to 120° C. under pressure, keeping this temperature for 1 h. The mixture is cooled to 50° C., added with 7.7 kg of 30% (w/w) sodium hydroxide, then gradually cooled to 40° C. in 2 h. After a further 4 h at 40° C. the mixture is cooled to 20° C. and pH is adjusted to 5.5 with hydrochloric acid. The resulting solution is loaded on 160 L of R&H Amberlite 1600 adsorbing resin, feeding the eluate to a nanofiltration unit equipped with Desal DK4040 membrane. After loading, elution is carried out with 800 L of water at 40° C., collecting again the eluate in the nanofiltration unit tank. During the elution or at the end, the nanofiltration unit is operated until the volume of the solution contained in the unity is reduced to about 200 L. By this way, concentration as well as elimination of most sodium chloride contained in the eluted solution is achieved.

The resulting solution of N,N'-bis(2,3-dihydroxypropyl)-5-[(hydroxyacetyl)methylamino]-2,4,6-triiodo-1,3-benzenedicarboxamide, which will be referred to in the following as solution A, contains 80 kg of the desired product, about 0.05 mol/L of organic ionic impurities (carboxylic aromatic acids) and 0.03 mol of inorganic salts (mainly NaCl).

200 kg of 40% (w/w) solution A are fed at a flow rate of 40 L/h to the unit described in the example of WO 97/30788, loaded with the same amounts of the same ion exchangers, previously regenerated according to the same method as in the example.

The eluate unit is equipped with a conductivity analyzer and with a photometer for the measurement of absorbance at 280 nm, to detect the presence of the organic product in the eluate. The eluate is discarded until the absorbance of the eluate starts raising quickly, evidencing the presence of the concerned organic product.

From this point, the eluate is collected in a tank until exhaustion of solution A. During the recovery of this fraction, which contains most organic product, conductivity remains below 0.1 $\mu$S/cm.

When solution A is exhausted, the mixed bed is washed with 30 L of water at the same flow rate and finally again with 150 L of water at a flow rate of 100 L/h, always collecting the eluate in the same product fraction tank.

Conductivity of the eluate is very low also during this step, except for a slight peak of conductivity, with maximum at 20 $\mu$S/cm, at the end of the low flow rate washing, likely due to osmotic effects immediately after the peak of the product.

The fraction corresponding to the desalted product, which is free form chlorine ions and carboxylic acids, is thermally concentrated to a thick residue containing 15% of water. The product is then recovered in substantially pure form by addition of absolute ethanol at the reflux temperature, cooling and filtration.

Example 2

Alternative Preparation of Compound (VII)

A) Preparation of 5-Hydroxy-1,3-benzenedicarboxylic Acid Butyl Diester 920 g of n-butanol and 583 9 of 5-hydroxy-1,3-benzenedicarboxylic acid are loaded in the esterification reactor, under nitrogen. 32 g of p-toluenesulfonic acid monohydrate are added under stirring. The resulting suspension is heated to reflux of the solvent, pressure is gradually decreased to 350 mbar to keep the temperature of the reaction mixture from 93 to 97° C. These conditions are kept for 7 hours, removing the formed water by azeotropical distillation. After completion of the reaction the solution is cooled to 50° C.

B) Preparation of N,N'-Bis-(2,3-dihydroxypropyl)-5-hydroxy-1,3-benzenedicarboxamide The solution of the compound prepared at step A) is added with 1305 g of isoserinol, pressure is decreased to 240 mbar, heating to 95° C. The reaction is continued for 12 hours, gradually decreasing pressure to 30 mbar.

After completion of the reaction the final solution is diluted with about 2800 g of water and purified through two columns connected in series containing respectively a strongly acidic ion exchange resin to remove the isoserinol excess and a weakly basic ion exchange resin to remove the anionic impurities. The product is eluted with water.

The eluate from the column is concentrated to standard volume. Sodium hydroxide is added to obtain the solution of the corresponding sodium salt.

4200 g of a 25% solution containing 1051 g of the desired compound are thereby obtained.

Isoserinol is recovered from the cationic resin as described in Example 1.

C) Preparation of 2-Chloro-N-methyl-acetamide

Condensation between 784 9 (6.4 mol) of ethyl chloroacetate and 549 9 (7.1 mol) of monometylamine (40% aqueous solution) is carried out in reactor kept at −5° C. After completion of the amine addition, said temperature is kept for a further 30 minutes.

The mixture is diluted with 957 g of water and pH is adjusted to acidic values (3.5<pH<5). The solution is then thermally concentrated under reduced pressure to a residue of about 1100 g. The weight is restored by addition of about 1570 g of demineralized water to obtain about 1970 g of a 30% aqueous solution containing 674 g of 2-chloro-N-methylacetamide.

D) Preparation of N,N'-Bis(2,3-dihydroxypropyl)-2,4,6-triiodo-5-[2-(methylamino)-2-oxoethoxy]-1,3-benzenedicarboxamide.

4200 g of the solution of N,N'-bis-(2,3-dihydroxypropyl)-5-hydroxy-1,3-benzenedicarboxamide obtained at step B) are at the same time added with ICl (keeping temperature below 25° C.) and 30% sodium hydroxide to keep pH 7. The addition of ICl ends when the redox potential is stabilized at 500 mV. 5320 g of ICl and 2580 g of sodium hydroxide are loaded in total. After that, 10 g of sodium bisulfite are loaded to destroy the iodine excess and the potential decreases to −20 mV.

The resulting solution is then added with 1970 g of the 2-chloro-N-methylacetamide solution obtained at step C). The mixture is heated at 95° C. for 7 hours and pH is kept at 5.8 by addition of 30% sodium hydroxide. After cooling at 30–40° C., the suspension is filtered and the solid is washed with water. 3350 g of humid product are thereby obtained, containing 2025 g of the desired product.

Yield from 5-hydroxy-1,3-benzenedicarboxylic acid: 81.2%.

E) Preparation of Compound (I)

2000 g of the compound prepared at step D) are suspended in 8660 L of deionized water and refluxed. The suspension is added with 7 g of 30% w/w sodium hydroxide, then heated to 100° C. keeping this temperature for 2 h. The mixture is cooled to 50° C., adding 172 g of 30% w/w sodium hydroxide, and gradually to 40° C. in 2 h. After a further 4h at 40° C. the mixture is cooled to 20° C.

After completion of the reaction the solution is recycled to a column containing 1.13 L of a weakly acidic cationic resin to remove the sodium hydroxide present at the end of the reaction, until pH 5.5. The solution is then loaded on 3.55 L of R&H Amberlite 1600 adsorbing resin connected in series to the battery of four columns containing the ion exchange resin described in WO 98/56504. The resin volumes in the four columns are 2 L, 0.7 L, 0.47 L and 0.47 L, respectively.

The elution of the product from the resins is monitored spectrophotometrically.

As soon as absorbance starts rising, the eluate is collected in a reactor together with the subsequent water washings of the whole battery of columns.

The purified, desalted solution is thermally concentrated under reduced pressure to a thick residue containing 0.22 parts of water per part of product (w/w). The residue is then added under reflux with 5 parts (w/w) of absolute ethanol to recover the product.

What is claimed is:

1. A process for the preparation of N,N'-bis[2,3-dihydroxupropyl]-5[(hydroxyacetyl)methylamino]-2,4,6-triiodo-1,3-benzendicarboxylic comprising the following steps:

a) esterification of 5-hydroxy-1,3-benzenedicarboxylic acid n-butyl and acidic catalysis to give 5-hydroxy-1,3-benzenedicarboxylic acid n-butyl diester(VIII);

b) amidation of compond (VIII) with an isoserinol excess, to give an aqueous solution of N,N'-bis-(2,3-dihydroxypropyl)-5-hydroxy-1,3-benzene-dicarboxamide, which is optionally transformed in the sodium salt (III);

c) iodination of compound (III) with ICl, in stoichiometric amount of in a 1% excess, to give N,N'-bis-(2,3-dihydroxypropyl)-5-hydroxy-2,4,6-triodo-1,3-benzene-dicarboxamide (IV);

d) alkylation of compound (IV) with compound (IX), 2-chloro-N-methyl-acetamidc, in aqueous solution, to give N,N'-bis(2,3-dihydroxypropyl)-2,4,6-triiodo-5-[2-methylamino)-2oxocthoxy]-1,3-benzene-dicarboxamide (VII), which is used as humid product; finally, e) Smiles' rearrangement of compound (VII) in basic conditions and subsequent purification to give Iomeprol (I), according to the scheme:

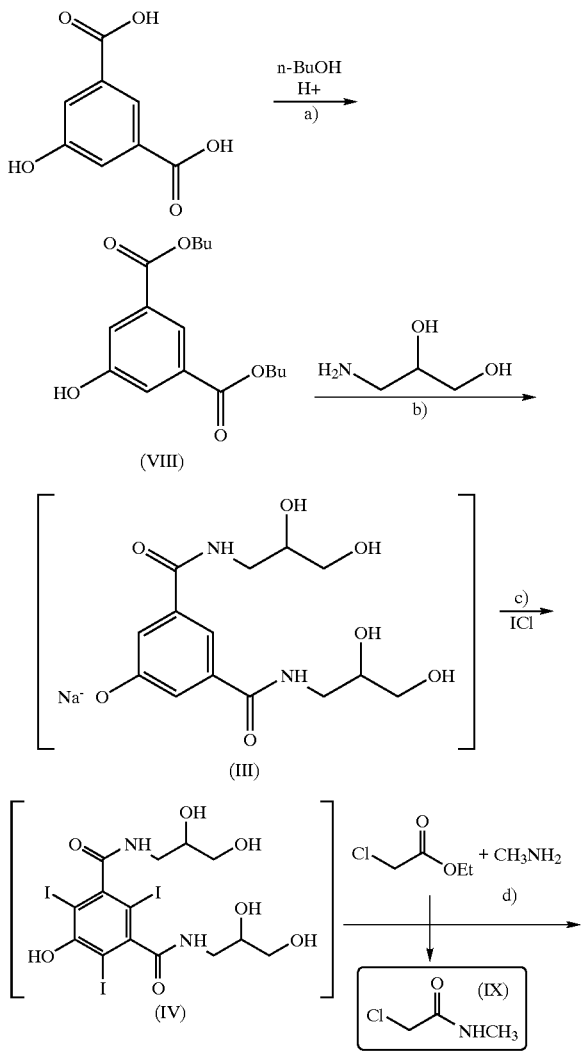

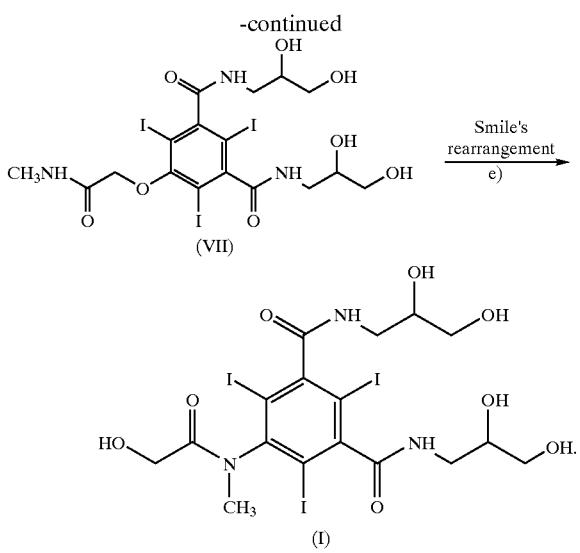

2. A process as claimed in claim 1, in which a catalytic amount of $H_2SO_4$ or p-toluenesulfonic acid, equivalent to 6% by mol, is used.

3. A process according to claim 1, in which compound (VIII) is recovered by direct crystallization form the final reaction mixture, which has previously been concentrated, by cooling.

4. A process according to claim 1, in which compound (VIII) is recovered by precipitation from an alkali aqueous solution, previously removing the organic solvent to a melted residue, which is subsequently treated with an inorganic base or ammonia aqueous solution, then subjected to controlled cooling to obtain compound (VIII) as partially crystalline solid.

5. A process as claimed in claim 4, in which compound (VIII) recovered as solid is redissolved in n-butanol to give a solution which is used as such in the subsuquent step.

6. A process as claimed in claim 1, in which, instead of recovering by precipitation compound (VIII), the reaction mixture is diluted with water, then purified from the isoserinol excess through a first column containing a strongly acidic cation exchange resin and from the ionic impurities through a second weakly basic anion exchange resin, connected in series with the first column.

7. A process as claimed in claim 1, in which step b) is carried out in mass in a 120% isoserinol excess, at a temperature of 90–95° C., for a time of about 12 hours, distilling off under vacuum the n-butanol formed in the reaction, treating the mass with water after completion of the reaction, to obtain an aqueous solution which is purified through a cation exchange resin and adjusted to pH 9–10 with NaOH to give the aqueous solution of the sodium salt corresponding to the compound (III).

8. A process as claimed in claim 5, in which before the reaction step (b) the solvent is removed to obtain compound (VIII) as a melted residue, which is finally treated under the conditions of claim 7.

9. A process as claimed in claim 7, in which the excess isoserinol is recovered and recycled in the process by elution form the resin with a diluted ammonia solution, the solution is concentrated to a residue and then purified by formation of isoserinol oxalate in ethanol solution and subsequent purification through a strongly acidic polystyrene matrix ion exchange cationic resin, isoserinol being recovered by elution with a diluted ammonia solution.

10. A process as claimed in claim 1, in which iodination is effected using ICl in neutral aqueous solution as iodinating agent, at pH ranging from 6 to 7, at room temperature, controlling by means of a potentiometer that the addition of iodinating agent is equivalent to the stoichiometric amount or to a slight excess (about 1%), to give a solution which is directly subjected to the subsequent alkylation step.

11. A process as claimed in claim 1, in which alkylation of compound (IV) with compound (IX) is carried out at neutral pH and at a temperature of 95° C., the alkylating agent being added in amounts of 1.8–2.2 mol per mol of substrate, at the end of the reaction the resulting suspension being cooled and fed to the recovery step of compound (VII).

* * * * *